(12) United States Patent
Postoyalko et al.

(10) Patent No.: US 7,682,572 B2
(45) Date of Patent: Mar. 23, 2010

(54) FROZEN TISSUE MICROARRAY

(75) Inventors: Andrew Postoyalko, North Yorkshire (GB); John Roberts, North Yorkshire (GB)

(73) Assignee: Covance, Inc., Princeton, NJ (US)

( * ) Notice: Subject to any disclaimer, the term of this patent is extended or adjusted under 35 U.S.C. 154(b) by 1315 days.

(21) Appl. No.: 11/153,488

(22) Filed: Jun. 16, 2005

(65) Prior Publication Data

US 2005/0282246 A1    Dec. 22, 2005

Related U.S. Application Data

(60) Provisional application No. 60/580,370, filed on Jun. 18, 2004.

(51) Int. Cl.
*B01L 3/00* (2006.01)
(52) U.S. Cl. .................................... 422/102
(58) Field of Classification Search .............. 422/102
See application file for complete search history.

(56) References Cited

U.S. PATENT DOCUMENTS 6,103,518 A   8/2000   Leighton et al.

2002/0137198 A1   9/2002   Mastorides et al.
2003/0038401 A1 *  2/2003   Lilischkis et al. ........... 264/248

FOREIGN PATENT DOCUMENTS

WO   WO 01/86250        11/2001
WO   WO 03044213 A2 *   5/2003

OTHER PUBLICATIONS

EPO International Search Report and the Written Opinion of the International Searching Authority; International Application No. PCT/US2005/021122; Dec. 23, 2005.
International Preliminary Report on Patentability issued in corresponding International Application PCT/US2005/02112, dated Jan. 4, 2007.

* cited by examiner

*Primary Examiner*—Walter D Griffin
*Assistant Examiner*—Bobby Ramdhanie
(74) *Attorney, Agent, or Firm*—McDermott Will & Emery LLP (57) ABSTRACT

A tissue microarray includes frozen tissue cores that extend from the top of the tissue microarray to a release. The release is a material from which embedding material of the tissue microarray can easily be removed. A stiffener is used with the release to maintain a flat shape of the release. The tissue cores may be formed from whole (i.e., paraffin-free) frozen tissue. A method and tool for manufacturing the tissue microarray are also disclosed.

23 Claims, 8 Drawing Sheets

FIG. 1

PRIOR ART

FROZEN TISSUE MICROARRAY

STATEMENT OF RELATED CASES

This case claims priority of U.S. provisional application No. 60/580,370, which was filed on Jun. 18, 2004, which is incorporated by reference herein.

FIELD OF THE INVENTION

The invention relates generally to analysis of tissues and, more specifically, to an improved method and apparatus for forming frozen tissue microarrays.

BACKGROUND OF THE INVENTION

Tissue microarrays increase the throughput of molecular analyses by simultaneously arraying proteins, nucleic acids, and other biomolecules. The tissue microarrays allow for the study of protein expression, antigen localization and molecular profiling of tissues samples. These tissue microarrays typically include cylindrical biopsies of human or animal tissue taken from already fixed paraffin-embedded tissue blocks or fresh frozen tissues. The cylindrical biopsies are the positioned into a tissue recipient microarray block, which can then be histologically prepared to produce sections for subsequent study. Tissue microarrays can provide a great number of tissues to be screened on a single slide and allow for rapid, large scale assessment of tissues compared to conventional histological techniques.

Figure 1:
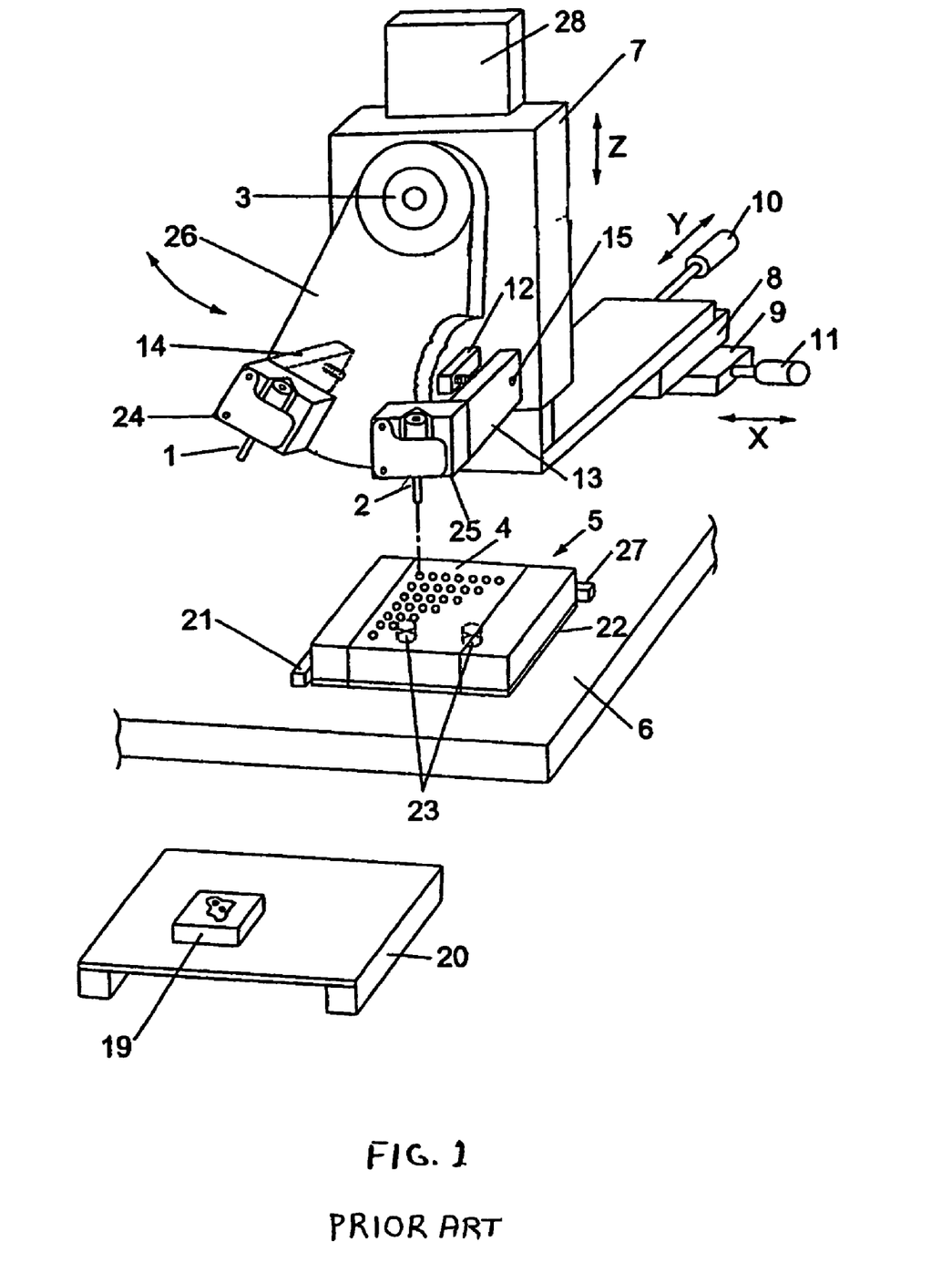
FIG. 1 is a perspective view of a conventional microarrayer.

In U.S. Pat. No. 6,103,518 to Leighton, incorporated herein by reference, Leighton describes a microarrayer instrument for automatically creating tissue microarrays. An example of this microarrayer is shown in FIG. 1. In the illustrated embodiment, a smaller recipient punch/needle 1 is used for making holes in a recipient block 4. A larger donor punch/needle 2, having an inner diameter corresponding to the outer diameter of the recipient punch 1, is used to obtain tissue core samples from the donor block 19. The donor punch 2 then embeds the tissue core samples into holes in the recipient block 4 formed by recipient punch 1. Each punch 1, 2 is provided with its own stylet/plunger for clearing material within the punch 1, 2, and each stylet has an outer diameter approximating that of the inner diameter of its respective punch 1, 2. At its greatest extension, the tip of the stylet slides past the tip of the punch 1, 2.

Blocks with recesses 24, 25 and clips are used to hold the respective punches 1, 2 on a pivot arm 26. The pivot arm 26 is pivotably mounted on a vertical carriage or slide 7 by a pivot bearing 3. The slide 7 moves vertically (z-axis) on a rail 28, which moves front to back (y-axis) on a horizontal slide 8 controlled by a drive 10. The horizontal slide 8 moves laterally (x-axis) on another slide 9 controlled by another drive 11. The slide 9 is affixed to a base plate 6.

Spacer bars 13, 14 are affixed to pivot arm 26, and each spacer bar 13, 14 is provided with an adjustment screw 15. Each screw 15 contacts an opposite side of the same stop 12, which is fixed with respect to the slide 7, thereby limiting the pivot movement and defining when the pivot arm is in either the first or second position. With the adjustment screws 5, the exact end of the travel can be set precisely. At one end of travel, the donor punch 2 is positioned in registry over a specific hole in the recipient block, and at the other end of the travel, the recipient punch 1 is precisely over the same location, assuming that the x- and y-axis drivers 10 and 11 have not been actuated.

Magnets 23 are fixed to the base 6 and hold a ferromagnetic plate 22 against the base plate 6 and against curbs or stops 21, 27. The ferromagnetic plate 22 is part of a recipient block holder 5, which holds recipient block 4. The holder 5, which includes the plate 22 and contains the block 4, can alternatively be easily removed from and reinserted to the same position on the base 6, or firmly held in place. The block 4 is formed from paraffin, or a like material, and individual recipient holes or an entire grid pattern of recipient holes may be cored into the recipient block 4 prior to harvesting samples from the donor block 4. The donor tissue block 19 rests on a removable bridge 20 that can be seated within stops 21, 27 or straddling the recipient block holder 22.

A problem associated with the creation of tissue microarrays using the apparatus and method described above is the removal of frozen embedding material from the recipient block using the recipient punch. As a needle of the punch is inserted into the embedding material, the embedding material immediately adjacent the needle is warmed by the needle and turns to liquid, and this liquefied embedding material adjacent the needle and frozen core of embedding material reduces the friction between the needle and frozen core. During an attempt to remove the frozen core of embedded material from the recipient block by withdrawing the needle, if insufficient friction exists between the frozen core of embedded material and the needle, the frozen core will slide relative the needle, and the frozen core will not be removed from the recipient block.

Another problem associated with the creation of tissue microarrays is the difficulty in creating cores in the recipient block that have a consistent depth. To solve this problem, the above-described microarrayer includes a depth stop kit that enables cores of an exact depth to be sampled from the donor block and the recipient block. This system allows paraffin-processed cores of an exact depth to be placed in holes having an identical depth. Since the paraffin-processed core is solid, the user of the instrument can easily determine when the core is fully inserted by detecting the resistance resulting from the solid bottom of the core contacting the bottom of the hole in the recipient block.

Paraffin-processed tissue cores, however, may not be the best option to demonstrate specific antigens. To solve this problem, whole frozen tissue cores are being used. However, the techniques used to control the size of the cores have problems when used with whole frozen tissues as the ability of an user to detect when a core fully inserted into a recipient block is compromised when the core is formed from whole frozen tissue. As the core is taken from the donor block, the material immediately adjacent the plunger may thaw slightly due to the temperature differential between the plunger and the frozen material. When thawing of the frozen material occurs, the user inserting the core into the recipient block does not detect exactly when the bottom of the core contacts the bottom of the hole in the recipient block because the thawed material flexes. Since the user cannot detect when the core is fully inserted, the core can be over-inserted into the hole in the recipient block, which results in the core being crushed. Since tissue is fragile and can be damaged by crushing, there is, therefore, a need for an improved tool and methodology for creating frozen tissue microarrays that reduces that incidence crushing of the tissue used to create the microarrays.

SUMMARY OF THE INVENTION

This and other needs are met by the present invention, which in accord with one aspect includes a tissue microarray having frozen tissue cores that extend from the top of the tissue microarray to a release. The release is a material from which embedding material of the tissue microarray can easily be removed. A stiffener is used with the release to maintain a flat shape of the release. The tissue cores may be formed from whole (i.e., paraffin-free) frozen tissue. By using the release, cores of frozen embedding material can be easily removed from the tissue microarray during the process of inserting donor tissue cores into the embedding material of the tissue microarray.

In another aspect of the invention, a process of the tissue microarray includes disposing a leveler on a partially filled mold. The leveler creates a flat surface in the embedding material upon which the release and the stiffener is positioned. The mold is then filled with embedding material, and after freezing, a recipient block is removed from the mold. A recipient punch is used to remove a core of embedding material from the recipient block, and when the recipient punch is removed from the recipient block, the core of embedding material detaches from the release, which creates a hole in the recipient block that extends to the release.

In yet another aspect of the invention, a donor punch inserts a frozen core of material into the hole in the recipient block. The donor punch includes a plunger that does not extend beyond the bottom of the needle. In this manner, when inserting the tissue core into the hole, the plunger does not compress the tissue core.

Additional advantages of the present invention will become readily apparent to those skilled in the art from the following detailed description, wherein only an exemplary embodiment of the present invention is shown and described, simply by way of illustration of the best mode contemplated for carrying out the present invention. As will be realized, the present invention is capable of other and different embodiments, and its several details are capable of modifications in various obvious respects, all without departing from the invention. Accordingly, the drawings and description are to be regarded as illustrative in nature, and not as restrictive.

In still another aspect of the present, invention, a moisture barrier is provided for protecting the micrometer and slide mechanisms of a microarrayer from moisture and frost damage during production of tissue microarrays.

BRIEF DESCRIPTION OF THE DRAWINGS

Reference is made to the attached drawings, wherein elements having the same reference numeral designations represent like elements throughout, and wherein.

DETAILED DESCRIPTION OF THE PREFERRED EMBODIMENTS

Figure 2:
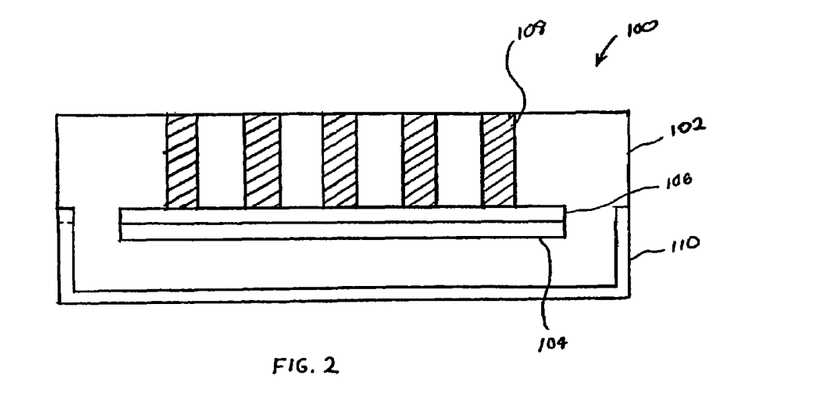
FIG. 2 is side sectional view of a tissue microarray according to an embodiment of the invention.

FIG. 2 illustrates a tissue microarray 100 according to an aspect of the invention. Consistent with conventional tissue microarrays, the tissue microarray 100 includes embedding material 102 positioned with a cassette 110, and the tissue microarray 100 is not limited as to a particular type of cassette 110. The cassette 110 is a fixture that is held by a tissue microarrayer (shown in FIG. 1) when tissue cores 108 are being inserted into the embedding material 102 of the tissue microarray 100. Many types of embedding material 102 exist, and the tissue microarray is not limited as to a particular embedding material 102. For example, the embedding material 102, also known as optimal cutting temperature compound (OCT), can formed from such materials as paraffin wax, nitrocellulose, polyvinyl alcohol, carbowax (polyethylene glycols), gelatin and agar.

The tissue microarray 100 also includes a release 106 and a stiffener 104. The release 106 and stiffener 104 may be a single piece or, as illustrated in FIG. 2, the release 106 and stiffener 104 may be separate. The release 106 is formed from a material from which the embedding material 102 can be removed with little force. As recognized by one skilled in the art, depending upon the particular type of embedding material 102 used to form the tissue microarray 100, many different types of materials are capable of performing this function, and the tissue microarray 100 is not limited as to a particular material so capable. Also, the release 106 may be a coating on the stiffener 104. However, in one aspect of the tissue microarray 100, the release 106 is formed from latex. The stiffener 104 acts to maintain the release 106 as a flat surface, and any material capable of performing this function is acceptable for use with the tissue microarray 100. In one aspect of the tissue microarray 100, the stiffener 104 is a paper strip that adheres to the latex release 106.

The height of the tissue cores 108 of the tissue microarray 100 extends from the top of the tissue microarray 100 to. the release 106. The tissue cores 108 can be made from any type of processed tissue used to form tissue microarrays. However, in one aspect of the invention, the tissue cores 108 are whole frozen tissue (i.e., paraffin-free).

Figure 3:
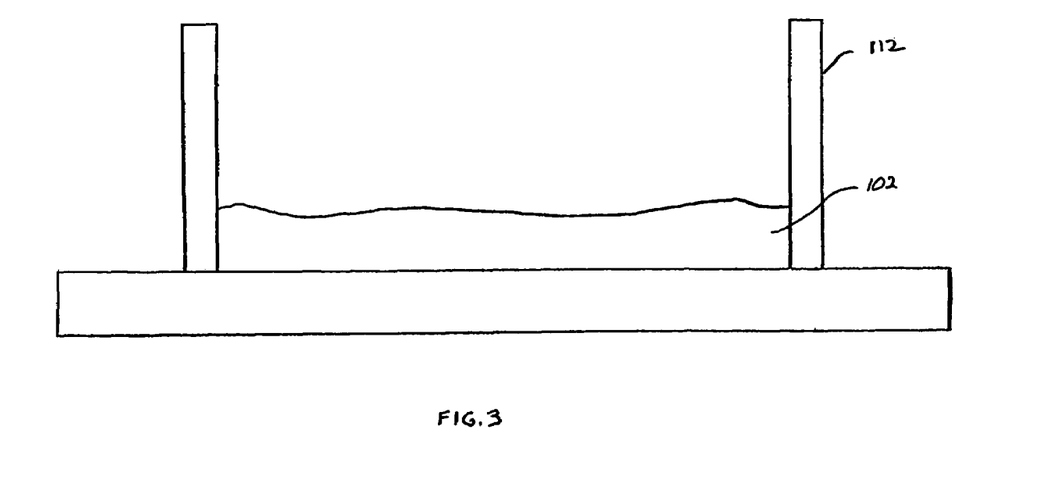
FIG. 3 is side sectional view of a step in the process of forming the tissue microarray after a mold is partially filled with embedding material.

A method of manufacturing the tissue microarray 100 is illustrated in FIGS. 3-11. In FIG. 3, a mold 112 is partially filled with an embedding medium 102. The mold 112 defines the outer periphery of the tissue microarray 100. Although not limited in this manner, the depth to which the mold 112 is filled is approximately equal to a height of the tissue cores 108 (shown in FIG. 1) to be inserted into the tissue microarray 100.

Figure 4:
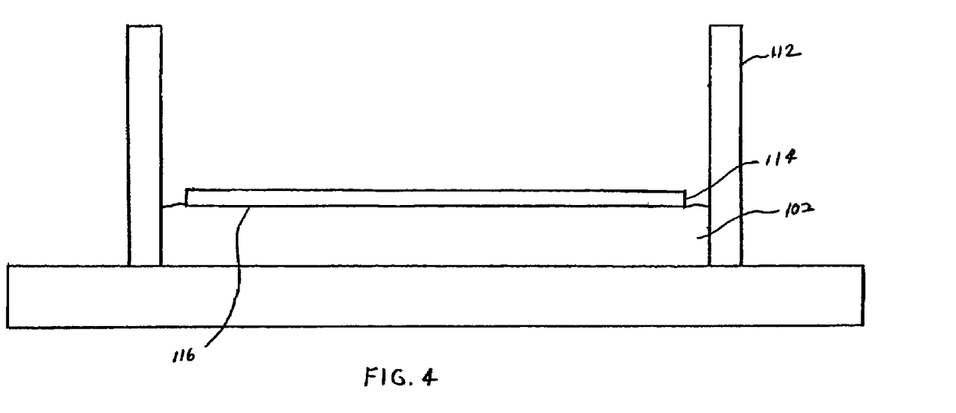
FIG. 4 is side sectional view of a step in the process of forming the tissue microarray after a leveler has been inserted into the mold.

In FIG. 4, a leveler 114 is inserted onto the embedding medium 102. The leveler 114 has a flat surface 116 that is placed against the embedding medium 102 to create a flat surface on the embedding medium 102. The leveler 114 is formed from a material that can be removed from the embedding medium 102 without excessively disturbing the embedding medium 102. In one aspect of the invention, the leveler 114 is formed from glass.

The leveler 114 may also be positioned on the embedding medium 102 such that the distance from the bottom of the mold 112 to the flat surface 116 of the leveler 114 is approximately equal to the height of the tissue cores 108 to be inserted into the tissue microarray 100. As would be recognized by one skilled in the art, many different types of devices/methods may be employed to maintain a desired spacing between the flat surface 116 of the leveler 114, and the invention is not limited as to a particular device/method to accomplish this spacing. For example, the leveler 114, when placed upon the embedding medium 102, can rest upon a spacer (not shown) within the mold 112 that maintains a predetermined distance between the bottom on the mold 112 and the flat surface 116 of the leveler 114.

Figure 5:
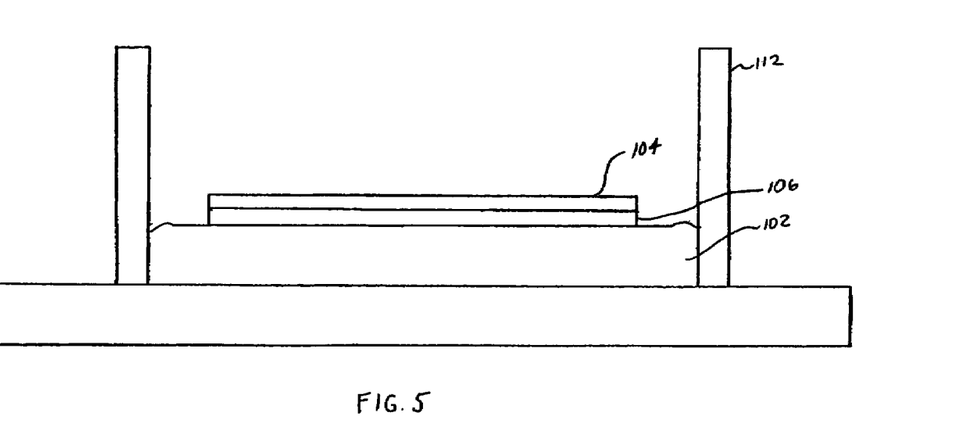
FIG. 5 is side sectional view of a step in the process of forming the tissue microarray after the embedding material has been frozen, the leveler removed from the mold, and a release/stiffener has been placed on the frozen embedding material.

After the leveler 114 is placed on the embedding medium 102, the construct is frozen. The leveler 114 is then removed from the embedding medium 102, which leaves a flat surface on the frozen embedding medium 102. In FIG. 5, a combination release 106 and stiffener 104 is placed on the flat surface of the frozen embedding medium 102 with the release-side down. Prior to placement of the release 106 and stiffener 104 on the frozen embedding medium 102, the release 106 may be coated with liquid embedding medium 102 to aide the adhering of the release 106 to the frozen embedding medium 102.

Figure 6:
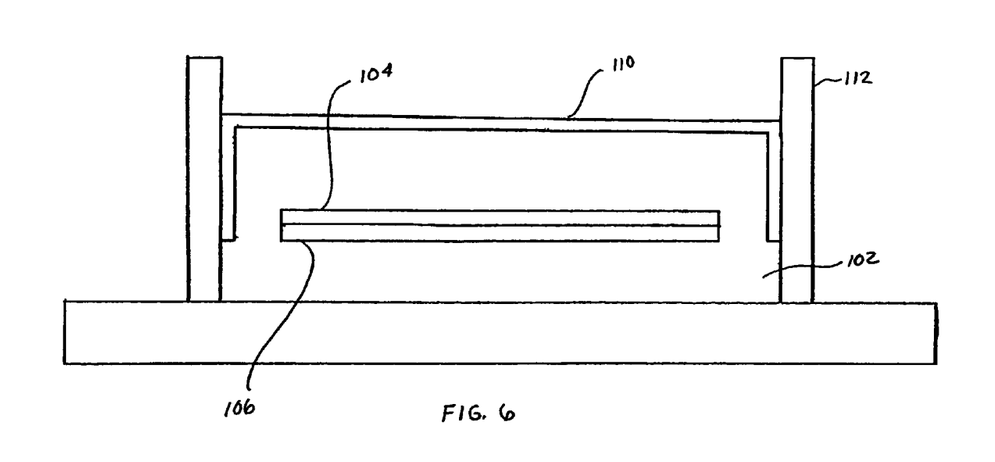
FIG. 6 is side sectional view of a step in the process of forming the tissue microarray after a cassette has been inserted into the mold and the mold filled with the embedding material.
Figure 7:
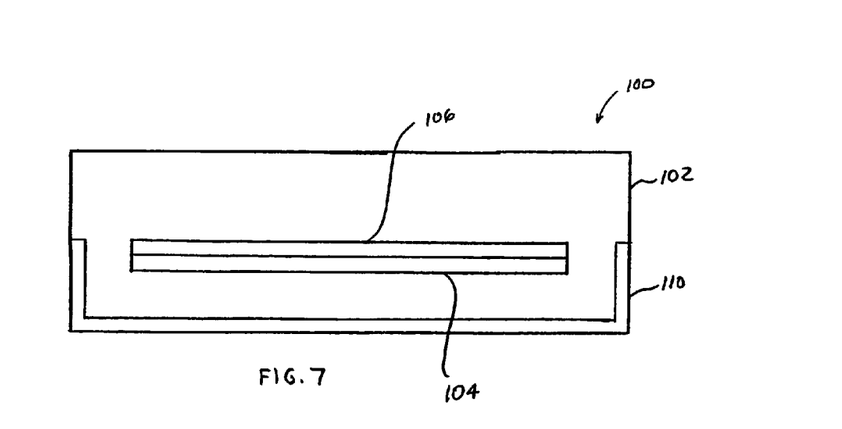
FIG. 7 is side sectional view of a step in the process of forming the tissue microarray after the embedding material has been frozen and a recipient block removed from the mold.

As shown in FIG. 6, once the release 106 and stiffener 104 is in place on the frozen embedding medium 102, a cassette 110 is placed within the mold 112 and the mold 112 is filled with embedding medium 102. After the cassette 110 and the remaining embedding medium 102 has been introduced into the mold 112, the assembly is again frozen. As shown in FIG. 7, once the assembly is frozen, the assembly is removed from the mold 112 and becomes a recipient block 100, which will later be transformed into a tissue microarray 100.

Figure 8:
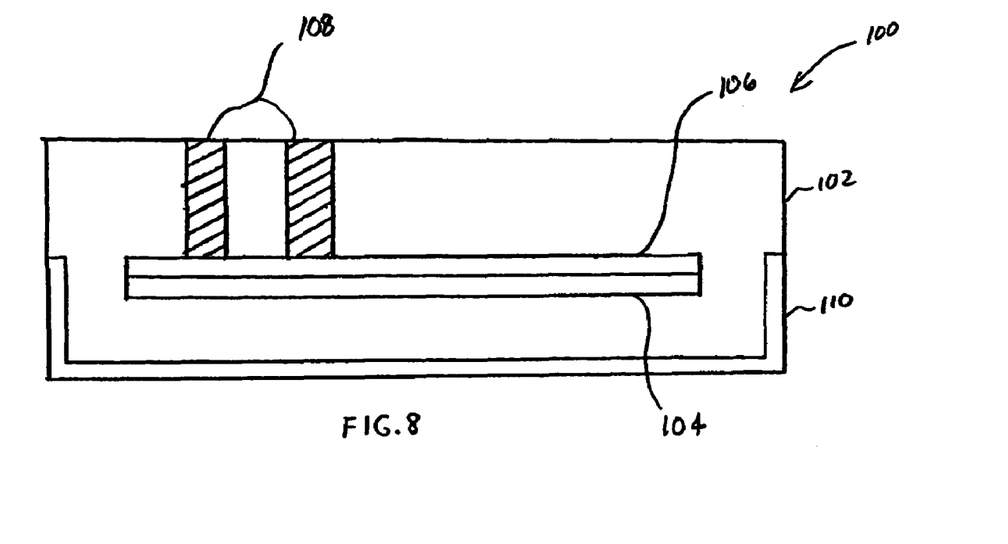
FIG. 8 is side sectional view of a step in the process of forming the tissue microarray after two tissue cores have been inserted into the recipient block.
Figure 9:
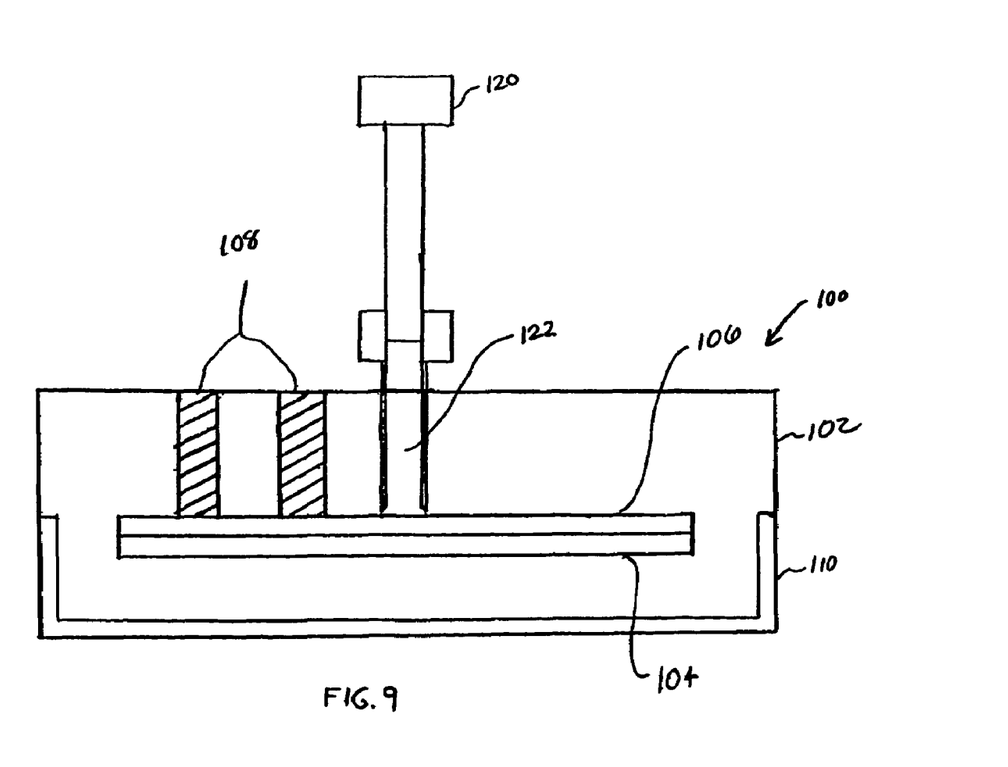
FIG. 9 is side sectional view of a step in the process of forming the tissue microarray after a recipient punch has been inserted into the embedding material of the recipient block.

The formation of the tissue microarray 100 using a recipient block and a donor block is similar to conventional processes, such as the process described in U.S. Pat. No. 6,103,518, which was referred to above. Certain exceptions to the conventional process are described with reference to FIGS. 8-11. FIG. 8 illustrates a partially formed tissue microarray 100 having tissue cores 108 that extend approximately to the surface of the release 106. In FIG. 9, a recipient punch 120 is used to remove a core 122 of embedding material from the tissue microarray 100.

The recipient punch 120 reaches to a depth approximately equal to a depth at which the release 106 is positioned. Upon the removal of the recipient punch 120 from the tissue microarray 100 (not shown), the core 122 within the recipient punch 120 easily separates from the release 106. This separation of the core 122 from the release 106 occurs even if the recipient punch 120 does not extend completely to the release 106. In this manner, a consistent depth of the hole 124 (shown in FIG. 10) can be obtained.

Figure 10:
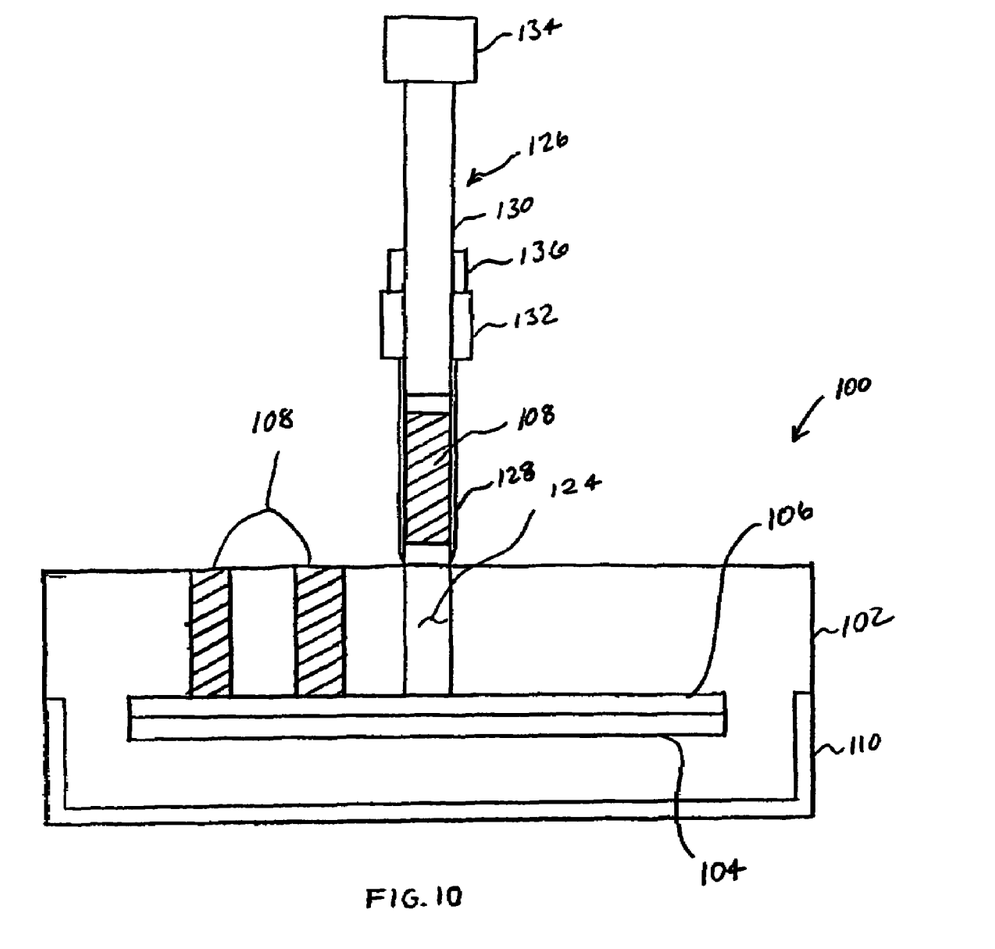
FIG. 10 is side sectional view of a step in the process of forming the tissue microarray after a core of embedding material has been removed from the recipient block and a donor punch has been positioned over a hold in the recipient block.

In FIG. 10, a tissue core 108 within a needle 128 of a donor punch 126 is positioned over the hole 124 in the tissue microarray 100. The bottom of the needle 128 is placed substantially even with the top surface of the tissue microarray 100 to maintain a known distance between the top surface of the tissue microarray 100 and a bottom surface of the plunger 130 of the donor punch 126.

Figure 11:
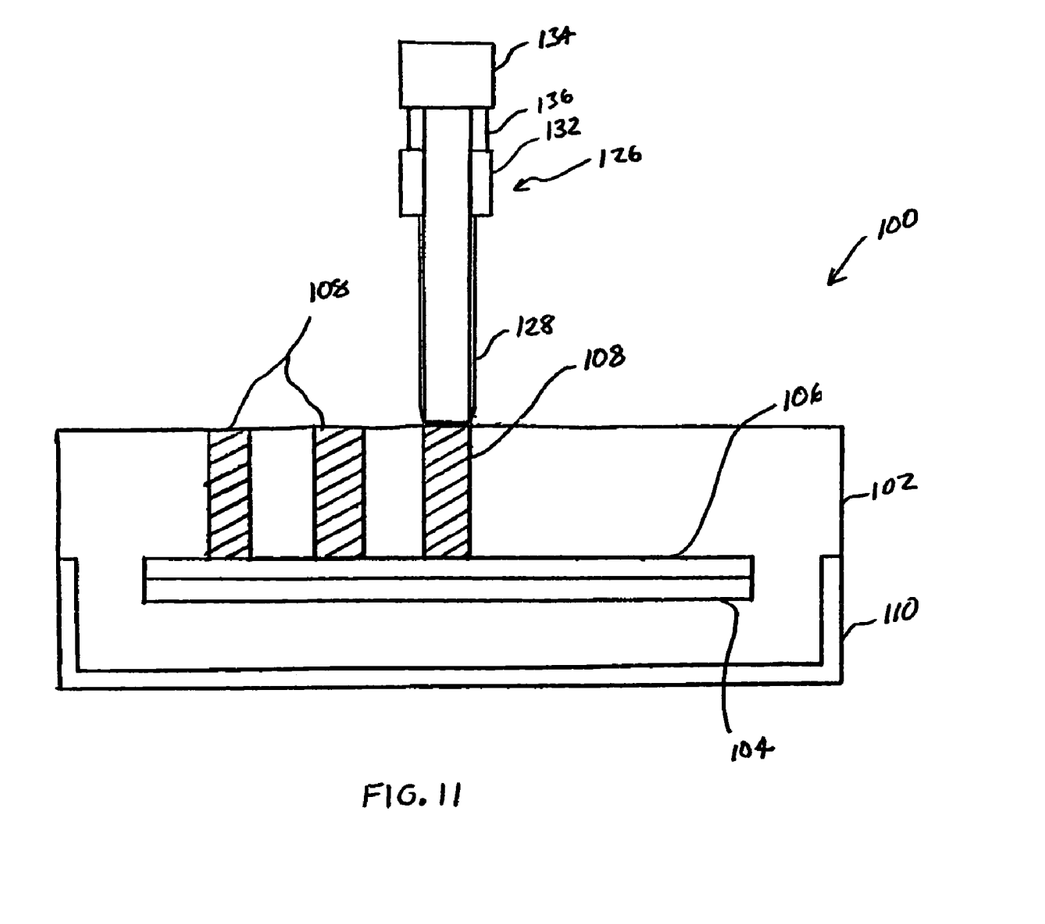
FIG. 11 is side sectional view of a step in the process of forming the tissue microarray after a frozen tissue core has been inserted into the hole in the recipient block using the donor punch.

In FIG. 11, the plunger 130 is depressed to insert the tissue core 108 into the hole 124. With a conventional donor punch, the bottom plunger is capable of extending beyond the bottom of the needle. In contrast, the donor punch 126 in one aspect of the present invention has a plunger 130 and a needle 128 whereby the plunger 130 extends to an end of the needle 128 but not beyond the end of the needle 128.

As evident to one skilled in the art, several modifications to a conventional donor punch exist that are capable preventing the plunger from extending beyond the end of the needle, and the invention is not limited as to a particular modification. For example, the donor punch can be shortened to prevent it from extending beyond the end of the needle. Another example, which is illustrated in FIG. 11, is to include a ring spacer 136 disposed between a top stop 134 of plunger 130 and a bottom stop 132 of the needle 128. The ring spacer 136 is sized such that travel of the plunger 130 in the donor punch 126 is stopped prior to the plunger 130 extending beyond the end of the needle 128.

The tissue core 108 is fully seated within the hole 124 and flush with the top surface of the tissue microarray 100 because the depth of the hole 124 is substantially equal to the size of the tissue core 108. Also, since the plunger 130 does not extend beyond the bottom of the needle 128, the plunger 130 does not extend into the hole 124. Thus, by providing a consistently-sized hole 124 and tissue core 108 that are substantially equal to one another, a known distance from the bottom of the hole 124 to the bottom of the plunger 130, and a plunger 130 does not extend beyond the bottom of the needle 128, the tissue core 108 can be fully inserted within the hole 124 using the plunger 130 without the tissue core 108 being compressed (and thereby damaged) by the plunger 130.

Although in one aspect of the invention, the plunger 130 is prevented from extending beyond the end of the needle 128, in another aspect, the plunger 130 extends slightly past the end of the needle 128. When a tissue microarray 100 is sectioned, the first few sections removed from the tissue microarray 100 are typically considered unusable for several quality factors. These factors include irregularities in the top surface of the tissue microarray 100, minor damage to the upper surface of the tissue core 108 due to contact with the plunger 130, and the tissue microarray 100 not being mounted perpendicular to the cutting blade during sectioning. These problems are particularly prevalent when the tissue core 108 has a diameter of 2 mm or less.

By enabling the plunger 130 to extend slightly past the end of the needle 128, the tissue core 108 is embedded deeper into the hole 124 and allows a gap between the top of the tissue core 108 and the top surface of the tissue microarray 100. This gap can be sized to correspond to the top portion of the tissue microarray 100 that experiences the most quality issues. In so doing, more usable sections can be obtained for a given length of a tissue core 108 because the first few sections removed from the tissue microarray 100 do not include the tissue core 108. For a tissue core 108 having a diameter of 2 mm or less, the gap is at least 0.5 mm, and in certain aspects, between about 0.5 mm and about 1.0 mm.

By placing a leveler 114, such as a glass plate, on the embedding material 102, a flat surface 116 can be formed on the embedding material 102 after the embedding material 102 is frozen and the leveler 114 is removed from the embedding material 102. On this flat surface 116, a release 106 and a stiffener 104 can be placed. The release 106 allows a core 122 of embedding material 102 adjacent the release 106 to be easily removed during a coring process, which prevents the core 122 from prematurely exiting the recipient punch 120 during the removal of the recipient punch 120 from the embedding material 102. A ring spacer 136 stops travel of a plunger 130 in a donor punch 126 past a particular point to prevent a tissue core 108 being inserted into the embedding material 102 from being crushed by the plunger 130.

In another aspect of the present invention, the arrayer mechanism is protected from moisture damage by a plastic sheet. When a microarrayer, such as the type shown in FIG. 1, is used for producing cryo-arrays, its front half (i.e., the area adjacent to plate 22) is typically covered with frozen carbon dioxide pellets to keep the recipient block 4 frozen. As a result, the entire arrayer becomes extremely cold, resulting in moisture in the air and in the operator's breath forming a frost build-up on the arrayer. This frost is undesirable because it can get pulled into micormeters 10, 11, potentially damaging their internal mechanisms. Moreover, the frost can build up on the runners 8, 9, impairing their smooth movement and causing the arrayer to stick.

Figure 12:
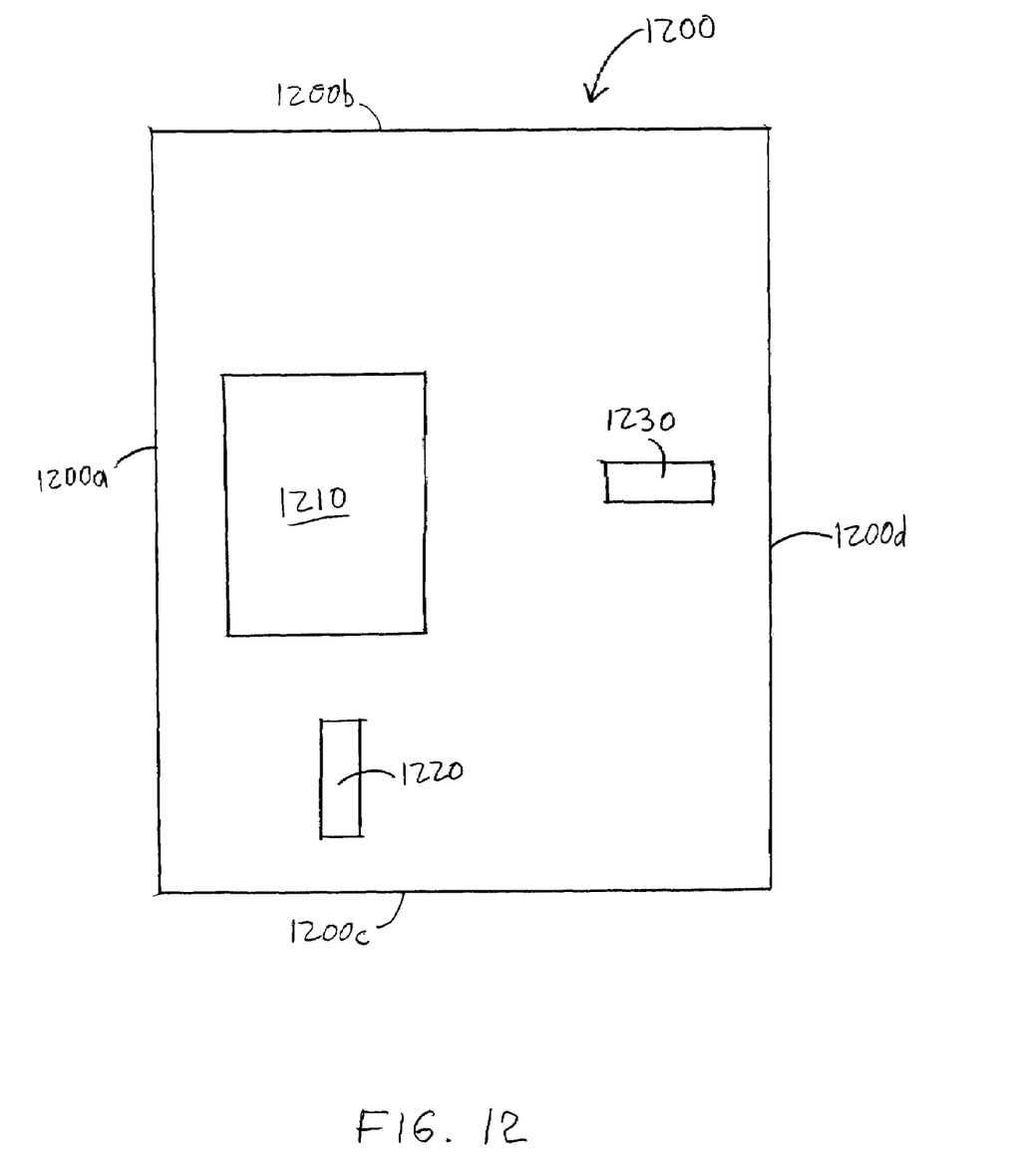
FIG. 12 is a plan view of a moisture barrier according to an embodiment of the present invention.

In this embodiment of the present invention, a moisture barrier is provided, such as a plastic sheet; for example a transparent polyethylene sheet, as shown in FIG. 12. The inventive moisture barrier 1200 has a rectangular hole 1210 in its front center, and two slots 1220, 1230, one to the right of the rectangular hole 1210 and a second to the rear of the hole 1210. Rectangular hole 1210 fits over the vertical side 7 of the microarrayer, and is attached around the base of slide 7, as by double-sided adhesive tape. The front edge 1200a of barrier 1200 is also attached, as by tape, allowing sufficient slack to allow x/y axis movement, to the base plate 6 behind the recipient block holder 27. The ends of the x and y micrometers 10, 11 are pushed through slots 1220, 1230, respectively, allowing access to their rotating knobs, while keeping the rest of their mechanism covered. Slots 1220, 1230 are loose-fitting enough to allow the operator to rotate the micrometers, and tight enough to keep out excess moisture. The side and rear edges 1200b-d of barrier 1200 are tucked under arrayer base plate 6, leaving sufficient slack to allow x/y movement.

The inventive moisture barrier 1200 does not create an airtight seal against moisture, but does restrict air flow sufficiently to prevent moisture and frost build-up on the micrometers and the runners that allow x/y movement.

The present invention may be practiced by employing conventional methodology and equipment. Accordingly, the details of such equipment and methodology are not set forth herein in detail. In the previous descriptions, numerous specific details are set forth, such as specific instructions, processes, etc., in order to provide a thorough understanding of the present invention. However, it should be recognized that the present invention may be practiced without resorting to the details specifically set forth.

Only an exemplary aspect of the present invention and but a few examples of its versatility are shown and described in the present disclosure. It is to be understood that the present invention is capable of use in various other combinations and environments and is capable of changes or modifications within the scope of the inventive concept as expressed herein.

What is claimed is:

1. A tissue recipient block for holding a tissue sample in a core extending from a top surface of the block to an internal surface of the block, the block comprising:

an embedding material extending between the top surface of the block and a bottom surface of the block below the internal surface of the block;

a release disposed at the internal surface of the block, the release being a material from which the embedding material can be separated, such that the core extends from the top surface of the block to the release; and a stiffener below the release for maintaining the release to have a substantially flat surface.

2. The tissue recipient block of claim 1, further comprising a cassette disposed below and in contact with the bottom surface of the embedding material for fixing the block to an apparatus for forming the core and positioning the tissue sample in the core.

3. The tissue recipient block of claim 1, wherein the embedding material is selected from the group consisting of paraffin wax, nitrocellulose, polyvinyl alcohol, carbowax, gelatin and agar.

4. The tissue recipient block of claim 1, wherein the stiffener and the release are unitary.

5. The tissue recipient block of claim 1, wherein the stiffener and the release are nonunitary.

6. The tissue recipient block of claim 4, wherein the release comprises a coating on the stiffener.

7. The tissue recipient block of claim 1, wherein the release comprises latex.

8. The tissue recipient block of claim 1, further comprising a plurality of cores extending from the top surface of the block to the release.

9. The tissue recipient block of claim 8, further comprising a plurality of tissue samples inside the cores, respectively, the tissue samples each comprising paraffin or paraffin-free whole frozen tissue, and substantially co-extensive with their respective core.

10. A method of manufacturing a tissue recipient block for holding a tissue sample in a core extending between a top surface of the block and an internal surface of the block, the method comprising:

partially filling a mold with a first amount of a liquid embedding medium;

leveling the exposed surface of the embedding medium to form a substantially flat surface on the embedding medium;

freezing the first amount of the embedding medium;

placing a release, from which the embedding medium can be separated, on the substantially flat surface of the first amount of the embedding medium;

placing a stiffener, for maintaining the release to have a substantially flat surface, on the release;

placing a cassette within the mold for forming a bottom of the tissue recipient block;

filling the remainder of the mold with a second amount of the liquid embedding medium; and freezing the first and second amounts of the embedding medium.

11. The method of claim 10, comprising partially filling the mold with the first amount of embedding material such that a depth to which the mold is filled is approximately equal to a height of the core.

12. The method of claim 10, comprising placing a leveler having a flat surface on the embedding medium such that a distance from the bottom of the mold to the flat surface of the leveler is approximately equal to a height of the core.

13. The method of claim 12, comprising resting the leveler on a spacer to maintain a predetermined distance between the bottom of the mold to the flat surface of the leveler.

14. The method of claim 10, comprising coating the release with liquid embedding medium prior to placing the release.

15. The method of claim 10, comprising selecting the embedding medium from the group consisting of paraffin wax, nitrocellulose, polyvinyl alcohol, carbowax, gelatin and agar.

16. The method of claim 10, wherein the release comprises latex.

17. The method of claim 10, further comprising:

removing the recipient tissue block from the mold and inverting the block such that the cassette is at the bottom of the block;

inserting a hollow recipient punch into the top surface of the block to a depth approximately equal to a depth at which the release is positioned; and removing the recipient punch and a core of embedding medium from the block to form a hole in the block extending from the top surface of the block to the release.

18. The method of claim 17, further comprising:

positioning a tissue core within a needle of a hollow donor punch over the hole, such that a bottom surface of the needle is substantially even with the top surface of the block; and depressing a plunger of the donor punch to insert the tissue core into the hole such that the plunger does not extend beyond the end of the needle, and the tissue core extends from the top surface of the block to the release.

19. A tool for manufacturing a tissue recipient block for holding a tissue sample in a core extending from a top surface of the block to an internal surface of the block, the tool comprising:

a mold defining an outer periphery and top surface of the block;

a leveler having a flat surface for positioning against the exposed surface of a liquid embedding medium partially filling the mold, for forming a substantially flat surface on the embedding medium, wherein the leveler is removable from the embedding material after the embedding material has been frozen; and a cassette, discrete from the embedding material, that fits within the mold to define a bottom surface of the block.

20. The tool of claim 19, wherein the leveler comprises glass.

21. The tool of claim 19, further comprising a spacer inside the mold to maintain a predetermined distance between the bottom of the mold to the flat surface of the leveler.

22. A moisture barrier for a microarrayer, the moisture barrier comprising a plastic sheet for covering a slide mechanism of the microarrayer and having a first opening for accommodating a vertical slide of the microarrayer, a second opening for accommodating a micrometer knob, and a third opening for accommodating another micrometer knob;

wherein outer edges of the plastic sheet, and the edges of the first opening, are attachable to a base plate of the microarrayer; and wherein the plastic sheet is configured for allowing motion of the slide mechanism.

23. The moisture barrier of claim 22, comprising tape for attaching the edges of the plastic sheet and the edges of the first opening to the base plate.

\* \* \* \* \*